United States Patent
Dong et al.

(10) Patent No.: US 6,719,751 B2
(45) Date of Patent: *Apr. 13, 2004

(54) OSMOTIC DOSAGE FORM COMPOSED OF AN EXTRUDED POLYMER TUBE FORM

(76) Inventors: Liang-Chang Dong, 171 Leota Ave., Sunnyvale, CA (US) 94086; Patrick S.-L. Wong, 1533 Burlingame Ave., Burlingame, CA (US) 94010; Atul Devdatt Ayer, 931 Bautista Ct., Palo Alto, CA (US) 94303; Padmaja Shivanand, 870 E. El Camino Real #44, Mountain View, CA (US) 94039; Michael A. DesJardin, 670 Lambeth Ct., Sunnyvale, CA (US) 94087

( * ) Notice: Subject to any disclaimer, the term of this patent is extended or adjusted under 35 U.S.C. 154(b) by 0 days.

This patent is subject to a terminal disclaimer.

(21) Appl. No.: 10/281,025

(22) Filed: Oct. 24, 2002

(65) Prior Publication Data

US 2003/0055408 A1 Mar. 20, 2003

Related U.S. Application Data

(63) Continuation of application No. 09/656,495, filed on Sep. 7, 2000, now Pat. No. 6,491,683.

(51) Int. Cl.[7] .................................................. A61K 9/26
(52) U.S. Cl. ..................................... 604/892.1; 424/473
(58) Field of Search .......................... 604/890.1, 891.1, 604/892.1; 424/468, 472, 433

(56) References Cited

U.S. PATENT DOCUMENTS

| | | | |
|---|---|---|---|
| 3,845,770 A | | 11/1974 | Theeuwes et al. |
| 4,111,202 A | * | 9/1978 | Theeuwes ................... 128/260 |
| 4,285,987 A | | 8/1981 | Ayer et al. |
| 4,350,271 A | * | 9/1982 | Eckenhoff .................. 128/260 |
| 4,455,143 A | * | 6/1984 | Theeuwes et al. .......... 604/890 |
| 4,608,048 A | * | 8/1986 | Cortese et al. ............. 604/890 |
| 4,783,337 A | | 11/1988 | Wong et al. |
| 4,892,778 A | | 1/1990 | Theeuwes et al. |
| 5,000,957 A | * | 3/1991 | Eckenhoff et al. ........ 604/890.1 |
| 5,053,032 A | * | 10/1991 | Barclay et al. ........... 604/892.1 |
| 5,795,591 A | * | 8/1998 | Lee et al. .................... 424/473 |
| 5,830,502 A | | 11/1998 | Dong et al. |
| 6,491,683 B1 | * | 12/2002 | Doug et al. ............... 604/892.1 |

* cited by examiner

Primary Examiner—Harry B. Tanner

(57) ABSTRACT

A dosage form manufactured from an extruded polymer tube and method for manufacturing the dosage form are disclosed. The dosage form is preferably an osmotic dosage form and includes a therapeutic agent and an expandable composition contained within the lumen of the extruded polymer tube.

21 Claims, 2 Drawing Sheets

OSMOTIC DOSAGE FORM COMPOSED OF AN EXTRUDED POLYMER TUBE FORM

CROSS-REFERENCE TO RELATED APPLICATIONS

This application is a CON of Ser. No. 09/656,495 Sep. 7, 2000 U.S. Pat. No. 6,491,683.

This application claims the benefit of U.S. Provisional Application No. 60/152,678, filed Sep. 7, 1999.

FIELD OF THE INVENTION

The present invention relates to dosage forms containing an extruded polymer tube. More specifically, the invention relates to polymer tube forms prepared by extrusion for the manufacture of osmotic dosage forms for administration of a therapeutic agent.

BACKGROUND OF THE INVENTION

One focus of efforts to improve drug therapy has been directed to providing drug dosage forms that provide controlled release of drug to the environment of use. Examples of such delivery systems include delayed-release and sustained-release systems. A particular approach to providing sustained release dosage forms that has found commercial success involves osmotic delivery systems, as described, for example, in U.S. Pat. Nos. 3,845,770 and 3,916,899. Osmotic dosage forms, in general, utilize osmotic pressure to generate a driving force for imbibing fluid into an internal compartment formed, at least in part, by a semipermeable wall that permits free diffusion of fluid but not drug or osmotic agent(s), if present. Following administration of the dosage form to a suitable fluid environment, such as the gastrointestinal tract or other body cavity or body tissue, fluid imbibition results in a deliverable drug-containing formulation being released from within the compartment through a suitable exit means formed through the semipermeable membrane. The rate of drug release is determined by the osmotic driving force.

Osmotic systems may be manufactured by forming the active agent and other ingredients for the internal compartment, such as an osmagent and osmopolymer, into a solid or semisolid by ballmilling, calendaring, stirring or rodmilling and then pressing into a preselected shape. The semipermeable wall material is dissolved in an appropriate solvent such as acetone or methylene chloride and is then applied to the pressed shape by molding, air spraying, dipping or brushing a solvent-based solution of the wall material onto the shape (U.S. Pat. Nos. 4,892,778, 4,285, 987). Other methods for applying the semipermeable wall include an air suspension procedure, where the pressed shape is suspended and tumbled in a current of air and wall forming material (U.S. Pat. No. 2,799,241), and a pan coating technique. After application of the semipermeable wall to the pressed shape, a drying step is required and, then, suitable exit means for the active agent must be formed through the semipermeable membrane. Depending on the properties of the active agent and other ingredients within the internal compartment and the desired release rate for the dosage form, one or more orifices for active agent delivery are formed through the semipermeable membrane by mechanical drilling, laser drilling, or the like. The orifice may range in size from a single large orifice containing substantially an entire surface of the dosage form to one or more small orifices selectively located on the surface of the semipermeable membrane.

Dosage forms prepared by solvent-coating the semipermeable wall onto the pressed shape have been commercially successful, providing controlled and continuous release of various active agents to a variety of environments. There is, however, a need to improve the manufacture of the dosage forms. As mentioned above, the semipermeable wall is typically manufactured using an organic solvent such as acetone or methylene chloride. Manufacture of the wall via an organic solvent deposition process yields excellent membranes however there are disadvantages associated with the use of solvents. The solvents can be expensive, they are explosive, traces can be toxic and their use has a negative environmental impact. Further, after deposition of the semipermeable wall, the solvent must be removed by drying, requiring a further time-consuming processing step. After solvent removal, suitable exit means for the active agent must be provided by a drilling step requiring additional equipment and labor.

One approach to the manufacture of the above-described devices utilizing an injection molding process for manufacturing the semipermeable wall is described in U.S. Pat. No. 5,830,502. This process provides a dosage form prepared without the use of organic solvents. However, the injection molding process involves the use of specifically designed molds that can be expensive, as are the molding machinery and auxiliary equipment.

There is a remaining need to provide another approach for the manufacture of dosage forms having such a semipermeable wall. Ideally, this approach would reduce or eliminate some of the processing steps required by methods described above, such as solvent deposition of the semipermeable wall, solvent removal and drilling of suitable active agent exit means.

SUMMARY OF THE INVENTION

In one aspect, the present invention provides osmotic dosage forms and methods for manufacturing osmotic dosage forms having membranes that are essentially free of organic solvents. In this manner, problems associated with the storage, handling and use of such solvents are eliminated. In addition, the number of processing steps is reduced and processing time is decreased because the need for solvent drying is eliminated.

In another aspect, the present invention provides methods for manufacturing osmotic dosage forms having membranes that do not require a drilling step to form exit means for the therapeutic agent.

The invention is directed to osmotic dosage forms for delivery of a therapeutic agent comprising an internal compartment formed, at least in part, by a semipermeable wall that permits free diffusion of fluid but not therapeutic agent(s) or osmotic agent(s) wherein the semipermeable membrane comprises an extruded polymer tube. Disposed within the internal compartment is (i) a therapeutic agent and (ii) an expandable composition capable of absorbing biological fluid from an environment of use to thereby expand within the internal compartment and facilitate delivery of the therapeutic agent out of the internal compartment. The polymer tube circumscribes the internal compartment and is open at each end. Depending on the properties of the active agent and other ingredients within the internal compartment and the desired release rate for the dosage form, release of therapeutic agent may occur through either an open tube end (or ends) or through a suitably sized orifice, smaller than the open tube end, configured at the tube end(s). Such an orifice is formed, for example, by crimping or heat-sealing or the like, of the tube end to close the end except for a suitably sized orifice.

In certain embodiments, release of therapeutic agent occurs at both tube ends while, in other embodiments, release occurs at only one tube end. In these other embodiments, the tube end opposite to the tube end where therapeutic agent is released is preferably configured to be partially or completely closed to ensure that the adjacent component of the internal compartment remains in place within the internal compartment. Accordingly, the size of the polymer tube with respect to the size of the internal compartment is adapted to accommodate the need, when present, to close either or both of the tube ends.

In certain embodiments, the dosage form includes a first layer containing therapeutic agent adjacent one end of the polymer tube and a second layer containing the expandable composition adjacent the other tube end. If desired, additional layers containing therapeutic agent(s) may also be included in the internal compartment between the therapeutic agent layer adjacent one tube end and the expandable composition adjacent the opposite tube end. In these embodiments, therapeutic agent will be released from the tube end adjacent to the therapeutic agent layer(s) following administration of the dosage form. Accordingly, depending on the properties of the active agent and other ingredients within the internal compartment and the desired release rate for the dosage form, this tube end may be left open or may be closed to an extent that provides a suitably sized orifice for the delivery of the therapeutic agent(s) therethrough. The opposite tube end, adjacent to the expandable composition, is closed either completely or substantially completely such that the expandable composition is retained within the internal compartment and to ensure that the pushing force generated by the expansion of the composition is substantially directed towards the therapeutic agent layer(s).

In other embodiments, the dosage form includes a first layer containing therapeutic agent adjacent one end of the polymer tube and a second layer containing therapeutic agent adjacent the other tube end with the expandable composition disposed between the first and second layers of therapeutic agent. The first and second layers containing therapeutic agent may comprise the same or different therapeutic agents. If desired, additional layers containing therapeutic agent(s) may also be included in the internal compartment on either side of the expandable composition. In these embodiments, therapeutic agent(s) will be released from both ends of the polymer tube following administration of the dosage form. Accordingly, depending on the properties of the active agent and other ingredients within the internal compartment and the desired release rate for the dosage form, either or both of the tube ends may be left open or may be closed to an extent that provides a suitably sized orifice for the delivery of the therapeutic agent(s) therethrough.

In still other embodiments, the dosage form further includes a non-expandable, inert, hydrophobic layer within the internal compartment that is positioned adjacent to one of the tube ends and also adjacent to the expandable composition. For example, the expandable composition can take the form of a discrete layer sandwiched between the non-expandable layer on one side and a therapeutic agent layer on the other side such that the therapeutic agent layer is adjacent the other tube end. If desired, additional layers containing therapeutic agent(s) may also be included in the internal compartment between the therapeutic agent layer adjacent the tube end and the expandable layer. In these embodiments, therapeutic agent(s) will be released from just one end of the polymer tube following administration of the dosage form. Accordingly, depending on the properties of the active agent and other ingredients within the internal compartment and the desired release rate for the dosage form, the tube end adjacent to a therapeutic agent layer may be left open or may be closed to an extent that provides a suitably sized orifice for the delivery of the therapeutic agent(s) therethrough. The tube end adjacent to the nonexpandable layer is preferably closed to an extent sufficient to ensure that the nonexpandable layer remains in place within the internal compartment.

In still another embodiment, the extruded polymer tube is composed of a polycaprolactone copolymer selected from the group consisting of polycaprolactone dilactide copolymer, polycaprolactone diglycolide, polycaprolactone valerolactone and polycaprolactone decaloactone. In one preferred embodiment, the extruded polymer tube is composed of a polycaprolactone and polyalkyleneoxide polymer blend.

The present invention is further directed to methods for manufacturing the dosage forms herein described. The methods include extruding a polymer into a tube form for circumscribing an internal compartment having first and second open ends, the polymer tube providing a semipermeable wall that permits free diffusion of fluid but not therapeutic agent or osmotic agent(s) and introducing into the internal compartment (i) a therapeutic agent and (ii) an expandable composition capable of absorbing biological fluid, following administration of the dosage form, to thereby expand and force the therapeutic agent to be released from the dosage form through either an open tube end or through an orifice formed in a tube end.

Optionally, a further step of configuring either or both of the tube ends, may be required. Depending on the properties of the active agent and other ingredients within the internal compartment and the desired release rate for the dosage form i.e., either or both of the open tube ends may be configured to be partially or fully closed, as by crimping or heat-sealing or the like. The extent of closure is determined by the specific purpose which may be either to ensure that a component of the internal compartment adjacent to the tube end remains in place within the internal compartment or to provide a suitably sized orifice, smaller than the open tube end, for delivery therethrough of therapeutic agent from within the internal compartment.

In one embodiment of this aspect, the step of introducing includes (i) placing component layers as described above, i.e., therapeutic agent layer(s), an expandable layer and a non-expandable layer, if included, in a selected order within the extruded tube to ensure that the appropriate layers are adjacent the tube ends. If desired, some or all of the discrete component layers may initially be compressed into a multi-layer tablet using a tablet press device and the compressed multi-layer tablet is then introduced into the internal compartment of the extruded tube. The remaining component layers, if any, are then placed into the tube and the step of configuring the tube ends, if needed, is performed.

These and other objects and features of the invention will be more fully appreciated when the following detailed description of the invention is read in conjunction with the accompanying drawings.

DETAILED DESCRIPTION OF THE INVENTION

Dosage Form Composition

Figure 1:
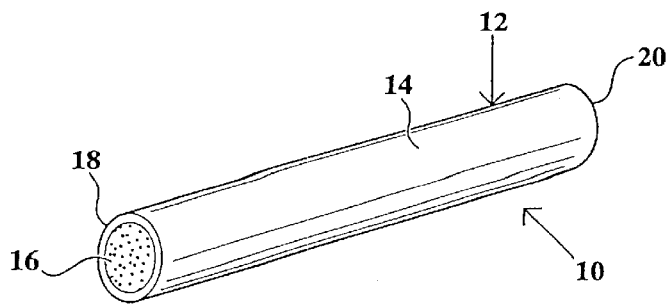
FIG. 1 is a perspective view of a dosage form having a semipermeable polymer outer tube wall, formed from an extruded polymer tube.

In accordance with the invention, an osmotic dosage form having an outer polymer tube formed by extrusion is shown in perspective view in FIG. 1. In FIG. 1, an osmotic device 10 is composed of an extruded polymer tube 12 with an outer tube wall 14. Tube 12 forms and defines an internal compartment 16 in communication with the tube ends 18, 20.

Polymer tube 12 is formed by extrusion of a semipermeable polymer that is selectively permeable to fluids in the environment of use, e.g., typically biological, aqueous-based fluids, and substantially impermeable to therapeutic agents and other compounds enclosed within tube 12. As set forth in more detail below, the semipermeable polymer can be a homopolymer, copolymer or a polymer blend, optionally including additives, plasticizers or processing agents, and use of the term "polymer" herein is intended to include these possible variations. The polymer can be extruded in such a way to form wall 14 with uniform properties across its dimensions, or to form wall 14 with micropores. Wall 14 when fabricated to be homogeneous and uniform in nature is selectively permeable to external fluid in the environment of use via the solution-diffusion process, where molecules of external fluid dissolve in and diffuse through wall 14 into internal compartment 16. When wall 14 is microporous in nature, molecules of external fluid enter and migrate into internal compartment 16 via the pores in the wall.

Polymers suitable for formation of polymer tube 12 include synthetic and naturally-occurring semipermeable materials. In a preferred embodiment, the polymer is a thermoplastic polymer and a detailed list of exemplary materials is set forth below. The semipermeable polymer wall is non-toxic and maintains its physical and chemical integrity during the delivery life of therapeutic agent from the device.

Internal compartment 16 of device 10 includes a therapeutic agent to be released from the device into the environment of use. Therapeutic agent is released from the internal compartment through open tube end 18. The therapeutic agent can vary from soluble to insoluble in the external fluid imbibed into the device. Optionally included in the internal compartment is an osmotic attractant or solute. Such a solute is included when the therapeutic agent to be released from the device has limited solubility in the imbibed external fluid (tissue fluid, gastric juices, tear fluid, etc.). The osmotic solute and/or the therapeutic agent are soluble in the fluid imbibed into internal compartment 16.

Exemplary osmotic solutes include compounds such as magnesium sulfate, magnesium chloride, sodium chloride, lithium chloride, potassium sulfate, sodium carbonate, sodium sulfite, lithium sulfate, calcium bicarbonate, sodium sulfate, calcium sulfate, potassium acid phosphate, calcium lactate, magnesium succinate, tartaric acid, soluble carbohydrates such as raffinose, glucose, mixtures thereof, and the like. The solute can be preset initially in excess in any suitable physical form such as particles, crystals, pellets, tablets, strips, film, granules, etc.

Figure 2:
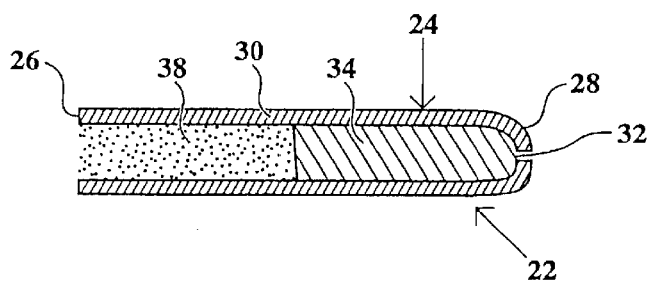
FIG. 2 is a cross sectional view along the length of an embodiment of a dosage form.

FIG. 2 is a cross sectional view along the length of an osmotic dosage form similar to that described in FIG. 1. Device 22 comprises an extruded polymer tube 24 having ends 26, 28 and forming a semipermeable outer wall 30. An internal compartment 32 is formed and defined by tube 24 and includes a therapeutic agent-containing layer 38 positioned to be adjacent to one of the tube ends. Therapeutic agent is released from the internal compartment through open tube end 26. The layer containing the therapeutic agent can optionally include an osmotic solute, such as those recited above, admixed with the agent along with other pharmaceutically acceptable excipients such as binders, lubricants, disintegrants, suspension agents, surfactants, diluents, stabilizers, antioxidants, colorants, plasticizers, and the like.

Also included in the internal compartment of the device is an expandable composition, indicated in FIG. 2 as element 34. The expandable composition is positioned to abut the therapeutic agent-containing layer 38 and to be adjacent to the opposing tube end. The expandable composition consists of a polymer having fluid imbibition properties, referred to herein as an osmopolymer. The osmopolymers are swellable, hydrophilic polymers that interact with water and aqueous biological fluids and swell or expand to a high degree, typically exhibiting a 2–50 fold volume increase. The osmopolymer can be non-crosslinked or crosslinked, but in a preferred embodiment are at least lightly crosslinked to create a polymer network that is too large and entangled to exit the device. Thus, in a preferred embodiment, the expandable composition is retained within the device during its operative lifetime.

Osmopolymers for use in the device can be of plant, animal or synthetic origin. The osmopolymers are hydrophilic polymers, and exemplary polymers include poly (hydroxyl-alkyl methacrylates) having a molecular weight of 30,000–5,000,000 Daltons; poly(vinyl pyrrolidone) having a molecular weight of from 10,000 to 360,000; anionic and cationic hydrogels; polyelectrolyte complexes; poly (vinyl alcohol) having a low acetate residual, crosslinked with glyoxal, formaldehyde or glutaraldehyde and having a degree of polymerization from 200–30,000; a mixture of methyl cellulose, cross-linked agar and carboxy-methyl cellulose; a mixture of hydroxypropyl methyl cellulose and sodium carboxymethylcellulose, hydroxy propyl methylcellulose and sodium carboxymethyl cellulose; a water insoluble, water swellable copolymer reduced by forming a dispersion of finely divided copolymer of maleic anhydride with styrene, ethylene, propylene, butylene or isobutylene crosslinked with a suitable agent; polymers of N-vinyl lactams; polyloxyethylene-polyoxypropylene gel; polyoxybutylene-polyethylene block copolymer gel; carob gum; polyacrylic gel; polyester gel; polyurea gel; polypeptide gel; polyamino acid gel; polycellulosic gel; polygum gel; hydrogels, such as Carbopol® acidic carboxy polymers, polymers of acrylic acid crosslinked with a polyallyl sucrose, known as carboxypolymethylene and carboxyvinyl polymers; Cyanamer® polyacrylamides; Polyox® polyethylene oxide polymers having a molecular weight of 810,000–5,000,000. Other suitable osmopolymers are set forth in U.S. Pat. No. 4,783,337, those portions of which are incorporated herein by reference.

With continuing reference to FIG. 2, in operation, the therapeutic agent is delivered from the device into the environment of use following imbibition of fluid by the osmopolymer in the expandable layer and/or the osmotic solute in the device. It will be appreciated that osmotic solute can be mixed with the therapeutic agent and/or with the osmopolymer to enhance fluid intake. As fluid is imbibed across the semipermeable wall of the device, a hydrated drug-layer composition containing the therapeutic agent, either in dissolved or particulate form depending on its solubility in the fluid, is formed within the internal compartment of the device. Fluid is also imbibed by the osmopolymer in the expandable layer, causing it to swell and push against the layer of therapeutic agent, driving the solution or suspension of therapeutic agent from the device via the adjacent tube end. The expandable layer, having a high molecular weight and being crosslinked, remains in place in the internal compartment of the tube and does not exit via the opposing end of the device. To ensure that the pushing force of the expandable layer is directed toward the therapeutic agent layer, the tube end adjacent the expandable polymer is closed, as by crimping or heat-sealing. The closing of the end can be complete or can be partial so long as sufficient to retain the position of the expandable polymer layer.

Figure 3:
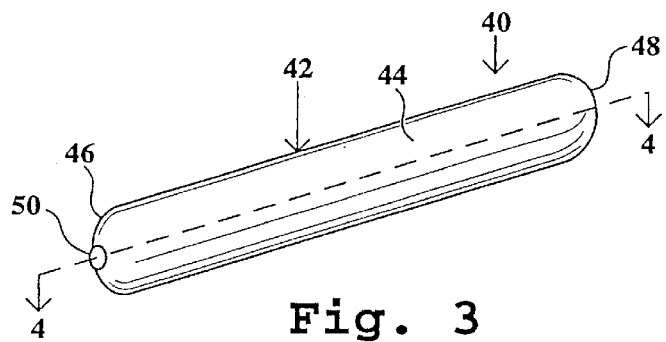
FIG. 3 is a perspective view of a dosage form in accord with the invention wherein both the tube ends are crimped to form orifices for delivery of therapeutic agent.

Another preferred embodiment of a device in accordance with the invention is shown in FIG. 3. In FIG. 3, a perspective view of an osmotic dosage form 40 is shown. Dosage form 40 is similar to that described above with respect to FIG. 2, and is composed of an extruded polymer tube 42 having an outer, semipermeable wall 44 and two ends, 46, 48. As described in more detail with reference to FIG. 4, below, ends 46, 48 of dosage form 40 are crimped inwards, partially closing the tube ends.

Figure 4:
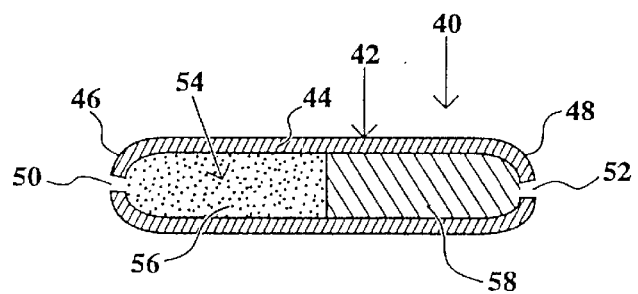
FIG. 4 is a cross sectional view along the length of a dosage form of FIG. 3.

FIG. 4 is a cross sectional view taken along the length of the dosage form 40 of FIG. 3, indicated at line 4—4 in FIG. 3. The internal compartment 54 formed by tube 42 includes, as discussed above, a layer of therapeutic agent 56 and an expandable layer 58. Ends 46, 48 of tube 42 are crimped inward towards the longitudinal axis of the device to partially close each end. Tube end 48, adjacent the expandable layer 58 within the internal compartment, is closed substantially completely to ensure that the expandable composition is retained within the internal compartment and that the pushing force generated by the expansion of the composition is substantially directed towards the therapeutic agent layer 56. Tube end 46, adjacent to the therapeutic agent layer, is closed to an extent that provides a suitably sized orifice 50 (also shown in FIG. 3) for the delivery of the therapeutic agent therethrough. As can be appreciated by those of skill in the art, the ends of the dosage form can be crimped to varying degrees to define orifices of various diameters. It will also be appreciated that each end can be crimped to a different amount if desired. Although a similar orifice 52 is also present at end 48, it is not intended that any release of therapeutic agent or expandable composition occur therethrough. It will also be appreciated that the end adjacent the expandable layer can be completely closed, if desired.

The embodiment of FIG. 4 shows the internal compartment of the tube comprising a single layer containing therapeutic agent 56 adjacent an expandable layer 58. It will be appreciated that multiple layers of the same or different therapeutic agent can be included, with one terminal layer abutting the expandable layer 58 and another terminal layer adjacent the tube end 46.

Figure 5A:
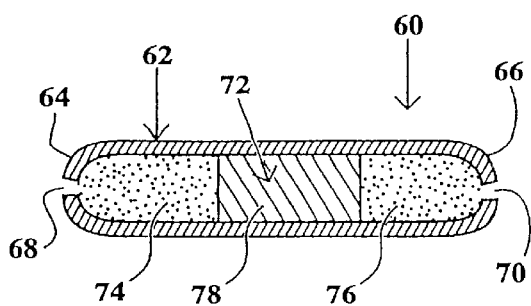
FIGS. 5A–5B are cross sectional views along the length of another embodiment of a dosage form wherein the expandable layer is disposed between first and second layers containing therapeutic agent and the tube ends of the dosage form are crimped to form orifices for delivery of therapeutic agent (FIG. 5A) or are left fully open (FIG. 5B)

FIG. 5A is a cross sectional view along the length of another embodiment of a dosage form showing a different arrangement of the components within the internal compartment of the device. Device 60 in FIG. 5A includes an extruded polymer tube 62 having first and second ends 64, 66. Tube 62 forms and defines an internal compartment 72 that includes first and second layers of therapeutic agent, 74, 76, adjacent each of the tube ends. Sandwiched between the layers of therapeutic agent is an expandable layer 78.

In operation, the expandable layer, composed of an osmopolymer as described above, swells and pushes on each of the layers containing the therapeutic agent, forcing the therapeutic agent in a deliverable formulation, such as a solution or suspension, to be released through both ends of the device following administration of the dosage form. Accordingly, depending on the properties of the active agent and other ingredients within the internal compartment and the desired release rate for the dosage form, either or both of the tube ends may be left open or may be closed to an extent that provides a suitably sized orifice for the delivery of the therapeutic agent(s) therethrough. FIG. 5A illustrates the device having both tube ends crimped inward to form delivery orifices 68, 70.

Figure 5B:
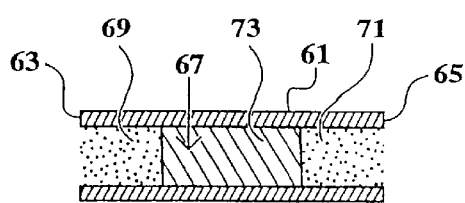

The device in FIG. 5B is similar to that described with reference to FIG. 5A except that, in this embodiment, the tube ends 63, 65 remain fully open and are not crimped. Polymer tube 61 defines an internal compartment 67 housing the layers containing therapeutic agent 69, 71 and an expandable push layer 73.

Figure 6A:
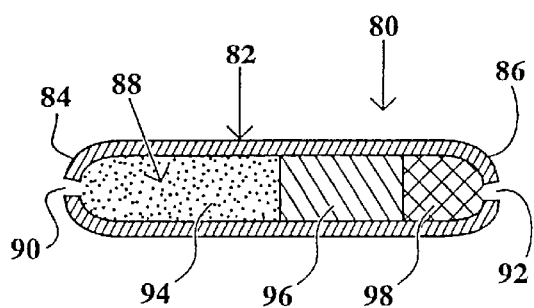
FIGS. 6A–6B are cross sectional views along the length of another embodiment of a dosage form in accord with the invention wherein the internal compartment includes a nonexpandable layer adjacent a tube end where that tube end is partially closed (FIG. 6A) or fully closed (FIG. 6B) to ensure that the nonexpandable layer is retained within the internal compartment of the dosage form.

Another embodiment of the device of the invention is shown in FIG. 6A. An osmotic device 80 composed of an extruded polymer tube 82 having ends 84, 86 and defining an internal compartment 88. Within internal compartment 88 is a layer of therapeutic agent 94, an expandable layer 96 composed of a hydrophilic, swellable, polymer and a nonexpandable layer 98. Nonexpandable, hydrophobic layer 98 is composed of an inert material which does not swell or expand in the presence of the external fluid which diffuses into the internal compartment through the semipermeable polymer tube wall of the device (or through the orifice 92 at tube end 86). Thus, the nonexpandable layer acts as an opposing force or counterweight to the expansion of the expandable layer as external fluid is imbibed into the device.

Materials suitable for the nonexpandable layer include virtually any inert material that is insoluble in the external fluid imbibed by the dosage form, for example, dibasic calcium phosphate, calcium carbonate, microfine waxes, stearic acid and magnesium stearate. These materials are generally water-insoluble and inert, and absorb little if any fluid entering the internal compartment of the device. Thus, they retain their original shape and rigidity and tend to remain in the device.

Upon administration, as the expandable layer 96 imbibes external fluid and increases in volume, the movement of the expandable layer during this volume increase is forced in the direction of layer of therapeutic agent 94, effectively pushing drug-laden solution or suspension out of the internal compartment. The inert, nonexpandable layer 98 functions to maximize expansion of the expandable layer in one direction, i.e., towards the layer of therapeutic agent 94. Ends 84, 86 of tube 82 are crimped inward towards the longitudinal axis of the device to partially close each end. Tube end 84, adjacent to the therapeutic agent layer 94, is closed to an extent that provides a suitably sized orifice 90 for the delivery of the therapeutic agent therethrough. Tube end 86, adjacent to the nonexpandable layer 98 within the internal compartment, is closed sufficiently to ensure that the nonexpandable composition is retained within the internal compartment to thereby ensure that the pushing force generated by the expansion of the expandable layer 96 is substantially directed towards the layer of therapeutic agent 94. Although a small orifice 92 may be present at end 86, as shown, it is not intended that any release of device components occur therethrough.

Figure 6B:
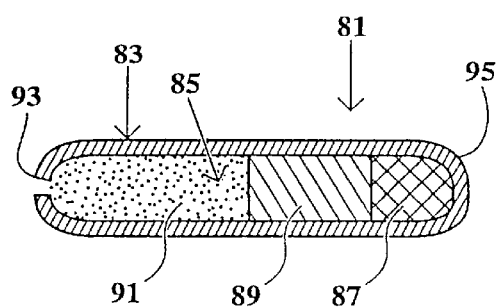

It will also be appreciated that the end adjacent the nonexpandable layer can be completely closed, if desired. The embodiment shown in FIG. 6B comprises polymer tube 83 defining internal compartment 85 housing the layers containing therapeutic agent 91, expandable layer 89 and nonexpandable layer 87. End 93 of tube 83 has been closed to form a delivery orifice for therapeutic agent. The device in FIG. 6B is similar to that described with reference to FIG. 6A except that, in this embodiment, the tube end 95, adjacent to the nonexpandable layer 87, is completely closed to ensure that the nonexpandable composition is retained within the internal compartment.

Figure 7A:
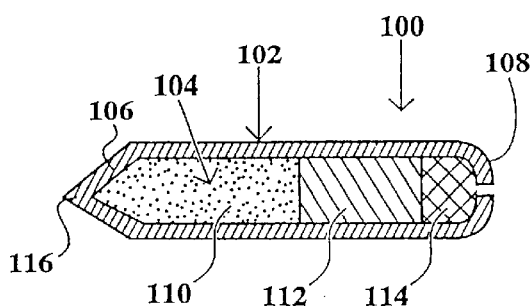
FIGS. 7A–7B are cross sectional views along the length of another embodiment of a dosage form, wherein the therapeutic agent is adjacent a tube end that is fully closed (FIG. 7A) and subsequently openable (FIG. 7B) or is formed partially closed (also FIG. 7B).
Figure 7B:
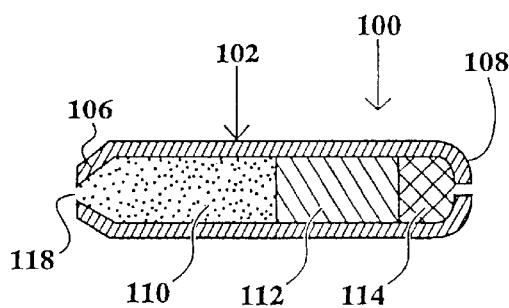

FIGS. 7A–7B are cross sectional views along the length of a dosage form according to another embodiment of the invention. In both FIGS. 7A and 7B, dosage form 100 is composed of an extruded polymer tube form 102 that forms and defines an inner lumen 104 and has two ends 106, 108. The inner tube lumen is charged with a layer of therapeutic agent 110, an expandable push layer 112 composed of an osmopolymer and a nonexpandable layer 114 as described above with respect to FIG. 6. In operation, as fluid permeates the wall of the polymer tube, expandable layer 112 swells. Expansion of layer 112 is forced in the direction of the therapeutic agent layer 110, as it is abutted at the opposing end by inert, nonexpandable layer 114. To ensure retention in the device, the tube end 108 adjacent the nonexpandable layer must be closed sufficiently for this purpose. Accordingly, this end may be nearly or fully closed, as shown above with reference to FIGS. 6A and 6B, respectively, or may be only partially closed as shown in FIGS. 7A and 7B provided such partial closure is sufficient to retain the nonexpandable layer within the device.

Delivery of therapeutic agent occurs through end 106. For this purpose, the tube end adjacent to the layer of therapeutic agent may be left open, as shown in FIG. 2, or may be partially closed to form a delivery orifice, as shown in FIG. 4. In the alternative embodiments shown in FIGS. 7A and 7B, end 106 of the tube is formed into a conical shape. As illustrated in FIG. 7A, end 106 is fully closed and, thus, requires a delivery orifice to be formed prior to administration of the device. Such a delivery orifice can be formed, for example, by snipping off a portion of the conical tip to form an exit orifice 118, as illustrated in FIG. 7B. This subsequent step of cutting the tip may be performed as a manufacturing step prior to marketing of the device. Alternatively, the device may be marketed as shown with a closed tip, as shown in FIG. 7A, and the subsequent step of forming the delivery orifice is performed by a health professional or patient at the time the device is to be administered. The latter case is particularly suited for dosage forms containing a liquid in the internal compartment of the tube.

The osmotic devices of FIGS. 1–7 can be used for delivering numerous agents at a controlled rate. The rate of release from the device can be controlled by selection of the polymer forming the outer tube wall as well as the thickness of the tube wall. The presence or absence of osmotic solutes within the inner lumen of the tube can also be varied to control the release rate. The osmotic devices also provide for low/high loading of agents of low solubility and their delivery at meaningful therapeutic amounts. While FIGS. 1–7 are illustrative of various osmotic devices that can be made according to the invention, it is to be understood these devices can take a wide variety of shapes, sizes and forms adapted for delivery of agents to various environments of use. For example, the devices can be shaped for use as buccal, implant, artificial gland, cervical, intrauterine, ear, nose, vaginal, penile and/or rectal devices.

Manufacture of the Dosage Form

The present invention is further directed to methods for manufacturing the dosage forms herein described. The methods include the steps of (a) extruding a polymer into a tube form for circumscribing an internal compartment having first and second open ends, the polymer tube providing a semipermeable wall that permits free diffusion of fluid but not therapeutic agent or osmotic agent(s) and (b) introducing into the internal compartment (i) a therapeutic agent and (ii) an expandable composition capable of absorbing biological fluid, following administration of the dosage form, to thereby expand and force the therapeutic agent to be released from the dosage form through either an open tube end or through an orifice formed in a tube end.

Optionally, a further step of configuring either or both of the tube ends, may be required. Depending on the properties of the active agent and other ingredients within the internal compartment and the desired release rate for the dosage form i.e., either or both of the open tube ends may be configured to be partially or fully closed, as by crimping or heat-sealing or the like. The extent of closure is determined by the specific purpose which may be either to ensure that a component of the internal compartment adjacent to the tube end remains in place within the internal compartment or to provide a suitably sized orifice, smaller than the open tube end, for delivery therethrough of therapeutic agent from within the internal compartment.

The method of the invention will now be described.

A. Extrusion of Polymer Tube

According to an important feature of the invention, the polymer tube forming the outer wall of the dosage form and defining the inner lumen is prepared by extrusion. As used herein, "extrusion" refers to a process of continuously forming an article, such as a tube, rod, strip or film, by pushing hot or cold material through a die. Conventional extruder equipment is known to those of skill in the art. The extrusion process can be a wet, dry or melt process. In the melt extrusion process, a polymer is heated above its melting point and extruded through a die designed to give the desired shape. Once extruded, the melt is cooled to solidify the polymer into the desired shape. In a dry extrusion process, a solution of the polymer is extruded through a desired orifice or die and is fed into a heated column to evaporate the solvent and solidify the polymer into the desired shape. In a wet extrusion process, a solution of the polymer is extruded through a die and quenched in a non-solvent for the polymer to coagulate the polymer into the desired shape. As used herein "extruded polymer" refers to an article prepared by an extrusion process.

In a preferred embodiment of the invention, the extruded polymer tube form is prepared via a melt extrusion process, where the desired polymer is fed into the extruder as a pellet, flake, powder, etc. The polymer or polymeric belend is propelled continuously along a screw through regions of high temperature and pressure which the polymer is melted and compacted to form a melt extrudate. The extrudate is pushed from the extruder through a die having the desired shape and dimensions to form a tube. The tube is cooled after extrusion and continuously taken up by a take-up device. It will be appreciated that the dimensions of the extruded polymer tube are variable, yet readily determined by those of skill in the art based on desired product characteristics. For example, the outer diameter of the extruded tube can be selected to conform to acceptable dimensions in the intended environment of use, such as an oral dosage form or a rectal insert. The inner diameter of the tube form can be selected to conform to the desired circumferential dimensions of the finished dosage form or to the circumferential dimensions of the preformed, pressed solid shape containing the therapeutic agent and expandable composition which is to be loaded into the tube form. Typical circumferential dimensions of such pressed solid shapes include, in inches, ¼, 9/32, 5/16, 3/8, 7/16 and 13/32. The thickness of the polymer tube form is determined in part by the desired inner and outer dimensions, but also by the polymer selected for use and its permeability to external fluid and the desired rate of release of therapeutic agent, as is known to those of skill in the art.

Polymers suitable for use in preparing the extruded tube form of the invention are preferably synthetic resins, including linear polycondensation resins, condensation polymerized resins, addition polymerized resins, such as polyamides, resins obtained from diepoxides and primary alkanolamines, resins of glycerine and phthalic anhydrides, polyvinyl resins, polymer resins with end-positions free or esterified carboxyl or carboxamide groups, for example with acrylic acid, acrylic amide, or acrylic acid esters, polycaprolactone, and its copolymers with dilactide, diglycolide, valerolactone and decalactone, a resin composition comprising polycaprolactone and polyalkylene oxide, composition comprising polycaprolactone and a polyakylene oxide such as polyethylene oxide, cellulose such as hydroxypropylmethylcellulose, hydroxyethylmethylcellulose, hydroxyethylcellulose, and hydroxypropylcellulose, copoly(butylene terephthalate-tetrahydrofuran), copoly(alkylene oxidemethylmethacrylate), and ethylene vinylacetate copolymer.

Some preferred and representative compositions include (percent (%) expressed is weight percent (wt %)) 10% to 99% of a thermoplastic polymer, and 1% to 90% of a different polymer with the total equal to 100%; 1% to 98% of a first thermoplastic polymer, 1% to 90% of a different, second polymer, and 1% to 90% of a different, third polymer, with all polymers equal to 100%. Other representative compositions provided by the invention comprise 20% to 90% of thermoplastic polycaprolactone and 10% to 80% of poly(alkylene oxide); a composition comprising 20% to 90% polycaprolactone and composition comprising 10% to 97% polycaprolactone, 10% to 97% poly(alkylene oxide), and 1% to 97% of poly(ethylene glycol) with all ingredients equal to 100%; a composition comprising 10% to 90% polycaprolactone, 10% to 80% polyalkylene glycol and 1% to 40% poly(ethylene glycol-co-propylene glycol) with all ingredients equal to 100%; a composition comprising 20% to 90% polycaprolactone and 10% to 80% of hydroxypropylcellulose with all ingredients equal to 100%; a composition comprising 1% to 90% polycaprolactone, 1% to 90% poly(ethylene oxide), 1% to 90% hydroxypropylcellulose and 1% to 90% poly(ethylene glycol) with all ingredients equal to 100%; 10% to 90% caprolactone-lactide copolymer and 10% to 80% poly(ethylene oxide) with all polymers equal to 100%; 10% to 90% caprolactoneglycolide and 10% to 80% poly(ethylene oxide) with all polymer materials equal to 100%; and 10% to 90% copoly(terephthalatetetramethylene glycol) and 10% to 80% ethylene vinylacetate with all polymer components equal to 100%.

One preferred composition is composed of a polycaprolactone of 63 wt %, a polyethylene oxide of 27 wt %, and a poly(ethylene glycol-copropylene glycol) of 10 wt %. Other preferred polymers are polystyrene polysulfonate, sold under the tradename Nafion®, and polycaprolactone (molecular weight 40,000–80,000 Daltons), sold under the tradename Tone® (Union Carbide).

B. Preparation of Internal Composition

1. Therapeutic Agent

As described above, the internal compartment formed and defined by the polymer is loaded with (i) a therapeutic agent and (ii) an expandable composition. The therapeutic agent can be admixed with the material forming the expandable composition or the therapeutic agent and the expandable composition can take the form of discrete layers enclosed in the internal compartment and abutting one another. Either or both layers can optionally include an osmotic solute.

Therapeutic agent as used herein refers to an agent, drug compound, composition of matter or mixture thereof which provides a therapeutic or beneficial effect. Such agents include pesticides, herbicides, germicides, biocides, algicides, rodenticides, fungicides, insecticides, antioxidants, plant growth promoters, plant growth inhibitors, preservatives, anti-preservatives, disinfectants, sterilization agents, catalysts, chemical reactants, fermentation agents, foods, food supplements, nutrients, cosmetics, drugs, vitamins, sex sterilants, fertility inhibitors, fertility promoters, microorganism attenuators and other agents that benefit the environment of use. As used herein, the terms further include any physiologically or pharmacologically active substance that produces a localized or systemic effect or effects in animals, including warm blooded mammals, i.e., humans and primates; avians; domestic household or farm animals such as cats, dogs, sheep, goats, cattle, horses and pigs; laboratory animals such as mice, rats and guinea pigs; fish; reptiles, zoo and wild animals; and the like. The active drug that can be delivered includes inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autocoid systems, the alimentary and excretory systems, the histamine system, and the central nervous system. Suitable agents may be selected from, for example, proteins, enzymes, hormones, polynucleotides, nucleoproteins, polysaccharides, glycoproteins, M. lipoproteins, polypeptides, steroids, hypnotics and sedatives, psychic energizers, tranquilizers, anticonvulsants, muscle relaxants, antiparkinson agents, analgesics, anti-inflammatories, local anesthetics, muscle contractants, antimicrobials, antimalarials, hormonal agents including contraceptives, sympathomimetics, polypeptides and proteins capable of eliciting physiological effects, diuretics, lipid regulating agents, antiandrogenic agents, antiparasitics, neoplastics, antineoplastics, hypoglycemics, nutritional agents and supplements, growth supplements, fats, ophthalmics, antienteritis agents, electrolytes and diagnostic agents. Examples of beneficial agents which this invention can be utilized with are prochlorperazine edisylate, ferrous sulfate, aminocaproic acid, mecamylamine hydrochloride, procainamide hydrochloride, amphetamine sulfate, methamphetamine hydrochloride, benzphetamine hydrochloride, isoproterenol sulfate, phenmetrazine sulfate, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione, erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, hydrocortisone, hydroxycorticosterone acetate, cortisone acetate, dexamethasone and its derivatives such as betamethasone, triamcinolone, methyltestosterone, 17-b-estradiol, ethinyl estradiol, ethinyl estradiol 3-methyl ether, prednisolone, 17-b-hydroxyprogesterone acetate, 19-norprogesterone, norgestrel, norethindrone, norethisterone, norethiederone, progesterone, norgesterone, norethisterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, captopril, mandol, quabenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, endlapriat, famotidine, nizatidine, sucralfate, etintidine, tertatolol, minoxidil, chlordiazepoxide, diazepam, amitriptyline, and imipramine. Further examples are proteins and protein-related compounds which include, but are not limited to, peptides, insulin, protease inhibitors such as indinivar, ritonavir, saquinavir, nelfinavir, VX-478 and SC-52151, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors as the prostaglandins, fertility promoters, growth factors, and human pancreas hormone releasing factor. It is to be understood that more than one therapeutic agent can be incorporated into the dosage form of this invention, and the use of the expressions therapeutic agent, active agent or drug in no way excludes the use of two or more such therapeutic agents, active agents or drugs. The therapeutic agent can be in a wide variety of chemical and physical forms, such as uncharged molecules, components of molecular complexes, pharmaceutically acceptable salts, therapeutic derivatives of the therapeutic agent such as ethers, esters, amides, etc., therapeutic derivatives of the therapeutic agent that are easily hydrolyzed by the body pH, and enzymes, are included in this invention.

The amount of therapeutic agent in the dosage form is a therapeutically effective amount, i.e., an amount necessary to produce the desired therapeutic response. In practice, this will vary widely depending upon the particular therapeutic agent, the site of delivery, agent-specific physical and chemical properties, the severity of the medical condition and other patient-specific parameters, and the desired therapeutic effect. Thus, it is often not practical to define a particular therapeutic range for a therapeutically effective dose of the therapeutic active agent incorporated into the dosage form. In general, however, the dosage form may contain 10 ng to 1.5 g of the therapeutic agent delivered at the rate of 0.4 ng to 65 mg per hour over 24 hours. The therapeutically active drugs are disclosed in Pharmacotherapy, Vol. 8, pp. 147–157 (1988); Drugs, Vol. 30, pp. 333–354 (1985); Remington's Pharmacological Basis of Therapeutics by Goodman and Gilman, 4th Ed. (1970) published by The Macmillan Company, London.

2. Internal Core Formation

In one embodiment, the device of the invention is manufactured by preparing a solid or semi-solid compressed multi-layer tablet of the therapeutic agent and any other components to be included in the internal compartment for insertion into an extruded tube form. For example, the therapeutic agent is mixed with an osmotic solute, if desired, and pressed into a solid having dimensions conforming to the internal compartment defined by the extruded polymer tube. In another embodiment, the therapeutic agent is mixed with the osmopolymer by ballmilling, rollmilling, stirring or calendering and pressed into such a solid form. In another embodiment, the therapeutic agent alone or in combination with an osmotic solute is pressed into a solid shape. Next, a layer of the expandable composition is pressed into a solid shape and layered adjacent the therapeutic agent. It will be appreciated that one or more layers containing therapeutic agent can be included. The compressed multi-layer tablet may have any suitable shape such as, e.g., a conventional tablet shape, a capsule shape with rounded ends or a capsule shape with blunt or bullet-shaped ends. Moreover, the layers may be arranged in any suitable manner within the compressed tablet. For example, for layers having an essentially rectangular shape, either the longer sides or the short sides may be arranged in contacting arrangement. Layering of materials is known to those of skill in the art and can be accomplished by conventional two-layer tablet press techniques or by custom multi-layer table press techniques.

Preparation of Dosage Form

The dosage form of the invention is prepared by extruding a polymer tube form via an extrusion process described above. A suitable length of the extruded tube form is cut and internal component layers as described above, i.e., therapeutic agent layer(s), an expandable layer and a nonexpandable layer, if included, are placed in a selected order within the extruded tube to ensure that the appropriate layers are adjacent the tube ends. If desired, as described above, some or all of the discrete component layers may initially be compressed into a multi-layer tablet using a tablet press device and the compressed multi-layer tablet is then introduced into the internal compartment of the extruded tube. The remaining component layers, if any, are then placed into the tube and the step of configuring the tube ends, if needed, is performed.

Alternatively, the dosage form is prepared via simultaneous extrusion of the tube form and loading of the therapeutic agent and expandable composition in the inner lumen of the tube form using an extruder capable of such an operation.

As described elsewhere, optionally, a further step of configuring either or both of the tube ends, may be required. Depending on the properties of the active agent and other ingredients within the internal compartment and the desired release rate for the dosage form i.e., either or both of the open tube ends may be configured to be partially or fully closed, as by crimping or heat-sealing or the like. The extent of closure is determined by the specific purpose which may be either to ensure that a component of the internal compartment adjacent to the tube end remains in place within the internal compartment or to provide a suitably sized orifice, smaller than the open tube end, for delivery therethrough of therapeutic agent from within the internal compartment.

The complete disclosures of the patents, patent documents, publications, etc., cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A dosage form comprising:
   an extruded polymer tube comprised of a polymer that is permeable to passage of biological fluids to form a semi-permeable outer tube wall, the polymer tube having an internal compartment and two open ends for communication between the internal compartment and an environment of use; and
   disposed within the internal compartment (i) a therapeutic agent and (ii) an expandable composition capable of absorbing the biological fluid to expand and force the therapeutic agent out at least one of the ends into the environment of use.

2. The dosage form of claim 1, wherein the dosage form further comprises a first layer of a therapeutic agent adjacent an end of the polymer tube and a second layer of a therapeutic agent adjacent the other tube end, and the expandable composition disposed between the first and second layers of therapeutic agent.

3. The dosage form of claim 2, wherein at least one tube end is closed to form an orifice through which the therapeutic agent is released into the environment of use.

4. The dosage form of claim 1, wherein the internal compartment further includes a nonexpandable layer disposed therein and adjacent one of the tube ends.

5. The dosage form of claim 4, wherein the expandable composition takes the form of a discrete layer in direct contact with the nonexpandable layer, and the therapeutic agent forms a layer in direct contact with the expandable layer and is adjacent the other tube end.

6. The dosage form of claim 5, wherein the tube end adjacent the therapeutic agent is closed to form an orifice through which the agent is released to the environment of use.

7. The dosage form of claim 6, wherein the tube end adjacent the nonexpandable layer is closed.

8. The dosage form of claim 1, wherein the extruded polymer tube is composed of a polycaprolactone copolymer selected from the group consisting of polycaprolactone dilactide copolymer, polycaprolactone diglycolide, polycaprolactone valerolactone and polycaprolactone decaloactone.

9. The dosage form of claim 1, wherein the extruded polymer tube is composed of a polycaprolactone and polyalkyleneoxide polymer blend.

10. A process for manufacturing a dosage form comprising:
    extruding a polymer into a tube form having an internal compartment and first and second open ends, the polymer forming a tube having a semipermeable wall that is permeable to passage of biological fluids; and
    introducing into the internal compartment (i) a therapeutic agent and (ii) an expandable composition capable of absorbing biological fluid from a surrounding environment of use to expand and force the therapeutic agent out at least one of the ends into the environment of use.

11. The process of claim 10 further comprising configuring one or both of the tube ends.

12. The process of claim 10, wherein the introducing includes (i) placing a first layer of therapeutic adjacent one tube end, (ii) depositing the expandable composition in contact with the first layer of therapeutic agent and adjacent the other tube end.

13. The process of claim 12, which further comprises closing one or both of the tube ends.

14. The process of claim 10, wherein the introducing includes (i) placing a first layer of therapeutic adjacent one tube end, (ii) depositing the expandable composition in contact with the first layer of therapeutic agent, and (iii) placing a second layer of therapeutic agent adjacent the other tube end in contact with the expandable composition.

15. The process of claim 14, which further comprises closing one or both of the tube ends to form an orifice through which the therapeutic agent is released to the environment of use.

16. The process of claim 10, which further comprises introducing (iii) a nonexpandable layer adjacent one of the tube ends.

17. The process of claim 16, wherein said introducing further comprises introducing a discrete layer of the expandable composition adjacent the nonexpandable layer and placing the therapeutic agent between the layer of expandable composition and the other tube end.

18. The process of claim 10, wherein the introducing further comprises introducing into the internal compartment a compressed multi-layer tablet comprising the therapeutic agent and the expandable composition.

19. The process of claim 18, wherein the compressed multi-layer tablet comprises: (i) a first layer of therapeutic agent, and (ii) a layer of expandable composition in contact with the first layer of therapeutic agent.

20. The process of claim 18, wherein the compressed multi-layer tablet comprises: (i) a first layer of therapeutic agent, (ii) the expandable composition in contact with the first layer of therapeutic agent, and (iii) a second layer of therapeutic agent in contact with the expandable composition opposite to the first layer of therapeutic agent.

21. The process of claim 18, wherein the compressed multi-layer tablet further comprises (iii) a nonexpandable layer disposed within the internal compartment such that the nonexpandable layer is adjacent one of the tube ends.

* * * * *